United States Patent [19]

Maurer et al.

[11] 4,200,637
[45] Apr. 29, 1980

[54] COMBATING ARTHROPODS WITH N,N-DIALKYL-O-(2-SUBSTITUTED-METHYL-PYRIMIDIN-4-YL)-CARBAMIC ACID ESTERS

[75] Inventors: Fritz Maurer; Rolf Schröder, both of Wuppertal; Ingeborg Hammann, Cologne, all of Fed. Rep. of Germany

[73] Assignee: Bayer Aktiengesellschaft, Leverkusen, Fed. Rep. of Germany

[21] Appl. No.: 960,153

[22] Filed: Nov. 13, 1978

[30] Foreign Application Priority Data

Nov. 25, 1977 [DE] Fed. Rep. of Germany ....... 2752613

[51] Int. Cl.² .......................................... C07D 239/20
[52] U.S. Cl. ...................................... 424/251; 544/319
[58] Field of Search ...................... 544/335, 309, 319

[56] References Cited

U.S. PATENT DOCUMENTS

| 2,694,712 | 11/1954 | Gysin et al. | 260/256.4 |
| 3,118,754 | 1/1964 | Nickell | 544/309 |
| 3,573,304 | 3/1971 | Eberle et al. | 544/335 |
| 3,950,353 | 4/1976 | Durant et al. | 544/335 |

FOREIGN PATENT DOCUMENTS 548752 10/1956 Italy ........................................ 544/309

*Primary Examiner*—Nicholas S. Rizzo
*Attorney, Agent, or Firm*—Sprung, Felfe, Horn, Lynch & Kramer

[57] ABSTRACT

N,N-Dialkyl-O-(2-substituted-methyl-pyrimidin-4-yl)-carbamic acid esters of the formula

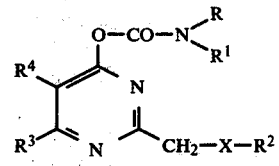

in which
R, $R^1$ and $R^2$ each independently is alkyl,
X is oxygen or sulphur,
$R^3$ is hydrogen or alkyl, and
$R^4$ is hydrogen, alkyl or halogen, or
$R^3$ and $R^4$ conjointly form an alkylene bridge, which possess arthropodicidal properties.

10 Claims, No Drawings

COMBATING ARTHROPODS WITH N,N-DIALKYL-0-(2-SUBSTITUTED-METHYL-PYRIMIDIN-4-YL)-CARBAMIC ACID ESTERS

The present invention relates to and has for its objects the provision of particular new N,N-dialkyl-0-(2-substituted-methyl-pyrimidin-4-yl)-carbamic acid esters which possess arthropodicidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It has already been disclosed that certain N,N-dialkyl-0-[2-alkyl-pyrimidin-4-yl]-carbamic acid esters, for example N,N-dimethyl-0-[2-isopropyl-6-methyl-pyrimidin-4-yl]-carbamic acid ester, possess insecticidal properties (see U.S. Pat. No. 2,694,712).

The present invention now provides, as new compounds, the N,N-dialkyl-0-pyrimidinyl-carbamic acid esters of the general formula

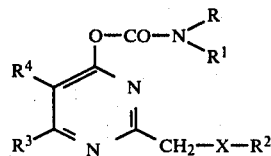 (I)

in which

R, $R^1$ and $R^2$, which need not be identical, each represents alkyl,

X represents oxygen or sulphur, $R^3$ represents hydrogen or alkyl, and $R^4$ represents hydrogen, alkyl or halogen, or $R^3$ and $R^4$ conjointly form an alkylene bridge.

Preferably, R, $R^1$ and $R^2$ each represent straight-chain or branched alkyl with 1 to 6 (especially 1 to 4) carbon atoms, $R^3$ represents hydrogen or straight-chain or branched alkyl with 1 to 8 (especially 1 to 5) carbon atoms and $R^4$ represents hydrogen, straight-chain or branched alkyl with 1 to 6 (especially 1 to 4) carbon atoms, chlorine or bromine, or $R^3$ and $R^4$ conjointly form an alkylene group with 3 to 5 carbon atoms.

Surprisingly, the N,N-dialkyl-0-pyrimidinyl-carbamic acid esters according to the invention exhibit a substantially greater insecticidal action than the N,N-dialkyl-0-[2-alkyl-pyrimidin-4-yl]-carbamic acid esters known from the prior art. The compounds according to the invention thus represent an enrichment of the art.

The invention also provides a process for the preparation of an N,N-dialkyl-0-pyrimidinyl-carbamic acid ester of the formula (I) in which (a) an N,N-dialkylcarbamic acid halide of the general formula

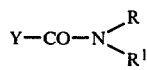 (II), in which

R and $R^1$ have the above-mentioned meanings and

Y represents halogen, especially chlorine, is reacted with a substituted 4-hydroxy-pyrimidine of the general formula

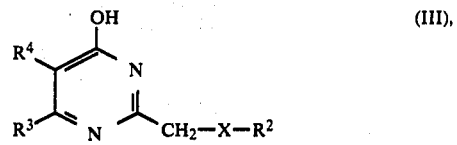 (III), in which $R^2$, $R^3$, $R^4$ and X have the above-mentioned meanings, if appropriate in the presence of an acid acceptor and, if appropriate, in the presence of a diluent, or (b) phosgene is reacted with a substituted 4-hydroxy-pyrimidine of the formula (III) and with a dialkylamine of the general formula

 (IV), in which

R and $R^1$ have the above-mentioned meanings, if appropriate in the presence of an acid acceptor and, if appropriate, in the presence of a diluent.

If, for example, the starting compounds used are 2-methoxymethyl-4-hydroxy-pyrimidine and, in accordance with process variant (a), N,N-dimethyl-carbamic acid chloride or, in accordance with process variant (b), phosgene and dimethylamine, the course of the reaction can be represented by the following equations:

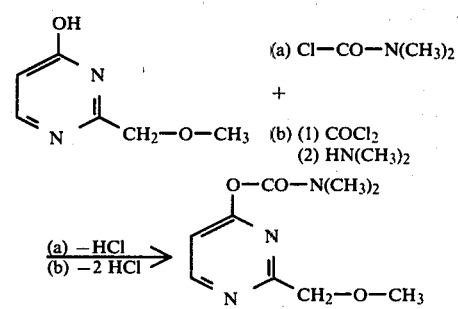

The 4-hydroxypyrimidines of the formula (III) usable as starting materials can be prepared in accordance with known processes: from 2-chloro-methyl-4-hydroxy-pyrimidines and alkali metal alcoholates in cases where X represents oxygen, and from 2-chloromethyl-4-hydroxy-pyrimidines and alkali metal salts of thiols in cases where X represents sulphur.

The following may be mentioned as examples of the 4-hydroxy-pyrimidines of the formula (III) which can be used as starting compounds: 2-methoxymethyl-4-hydroxy-, 2-methoxymethyl-4-hydroxy-5-methyl-, 2-methoxymethyl-4-hydroxy-6-methyl-, 2-methoxymethyl-4-hydroxy-5,6-dimethyl-, 2-methoxymethyl-4-hydroxy-5-methyl-6-ethyl-, 2-methoxymethyl-4-hydroxy-5-ethyl-6-methyl-, 2-methoxymethyl-4-hydroxy-5-methyl-6-n-propyl-, 2-methoxymethyl-4-hydroxy-5-n-propyl-6-methyl-, 2-methoxymethyl-4-hydroxy-5-methyl-6-isopropyl-, 2-methoxymethyl-4-hydroxy-5-isopropyl-6-methyl-, 2-methoxymethyl-4-hydroxy-5-methyl-6-n-butyl, 2-methoxymethyl-4-hydroxy-5-n-butyl-6-methyl-, 2-methoxymethyl-4- hydroxy-5-methyl-6-tert.-butyl-, 2-methoxymethyl-4-hydroxy-5-tert.-butyl-6-methyl-, 2-methoxymethyl-4-hydroxy-5-chloro-, 2-methoxymethyl-4-hydroxy-5-bromo-, 2-methoxymethyl-4-hydroxy-5-chloro-6-methyl-, 2-methoxymethyl-4-hydroxy-5-bromo-6-methyl-, 2-ethoxymethyl-4-hydroxy-, 2-ethoxymethyl-4-hydroxy-5-methyl-, 2-ethoxymethyl-4-hydroxy-6-methyl-, 2-ethoxymethyl-4-hydroxy-5,6-dimethyl, 2-ethoxymethyl-4-hydroxy-5-methyl-6-ethyl-, 2-ethoxymethyl-4-hydroxy-5-ethyl-6-methyl-, 2-isopropoxymethyl-4-hydroxy-, 2-isopropoxymethyl-4-hydroxy-5-methyl-, 2-isopropoxymethyl-4-hydroxy-6-methyl-, 2-isopropoxymethyl-5,6-dimethyl-, 2-isopropoxymethyl-4-hydroxy-5-chloro-6-methyl-, 2-isopropoxymethyl-4-hydroxy-5-bromo-6-methyl-, 2-methylthiomethyl-4-hydroxy-, 2-methylthiomethyl-4-hydroxy-5-methyl-, 2-methylthiomethyl-4-hydroxy-6-methyl-, 2-methylthiomethyl-4-hydroxy-5,6-dimethyl-, 2-methylthiomethyl-4-hydroxy-5-methyl-6-ethyl-, 2-methylthiomethyl-4-hydroxy-5-ethyl-6-methyl-, 2-methylthiomethyl-4-hydroxy-5-methyl-6-isopropyl-, 2-methylthiomethyl-4-hydroxy-6-methyl-5-isopropyl-, 2-methylthiomethyl-4-hydroxy-5-chloro-6-methyl-, 2-methylthiomethyl-4-hydroxy-5-bromo-6-methyl-, 2-methylthiomethyl-4-hydroxy-5-methyl-6-tert.-butyl-, 2-methylthiomethyl-4-hydroxy-5-tert.-butyl-6-methyl-, 2-methylthiomethyl-4-hydroxy-6-tert.-butyl-, 2-ethylthiomethyl-4-hydroxy-, 2-ethylthiomethyl-4-hydroxy-5-methyl-, 2-ethylthiomethyl-4-hydroxy-6-methyl-, 2-ethylthiomethyl-4-hydroxy-5,6-dimethyl-, 2-isopropylthiomethyl-4-hydroxy, 2-isopropylthiomethyl-4-hydroxy-5-methyl-, 2-isopropylthiomethyl-4-hydroxy-6-methyl- and 2-isopropylthiomethyl-4-hydroxy-5,6-dimethyl-pyrimidine, 2-methylthiomethyl-4-hydroxy-1,3-diaza-bicyclo(4,3,o)-nona-2,4,6-triene and 2-ethylthiomethyl-4-hydroxy-1,3-diazabicyclo-(4,3,o)-nona-2,4,6-triene.

Dimethyl-carbamic acid chloride and diethyl-carbamic acid chloride may be mentioned as examples of the carbamic acid halides of the formula (II) to be employed in accordance with process variant (a).

Suitable diluents in both variants are all inert organic solvents. As examples of these there may be mentioned hydrocarbons, such as benzene, toluene and xylene; chlorinated hydrocarbons, such as methylene chloride, chloroform or carbon tetrachloride as well as chlorobenzene or o-dichlorobenzene; ethers, such as diethyl ether and dibutyl ether; ketones, such as acetone, methyl ethyl ketone, methyl isopropyl ketone and methyl isobutyl ketone; and nitriles, such as acetonitrile and propionitrile.

The customary acid-binding agents can be used as acid acceptors in both variants. As examples of these there may be mentioned alkali metal carbonates and alkali metal alcoholates, such as sodium carbonate and potassium carbonate, sodium methylate and ethylate and potassium methylate and ethylate, as well as aliphatic, aromatic or heterocyclic amines, for example triethylamine, dimethylaniline, dimethylbenzylamine and pyridine.

In both variants of the process, the reaction temperature can be varied within a substantial range. In general, the reaction is carried out at from 0° to 150° C., preferably from 20° to 100° C.

In both variants, the reaction is in general carried out under normal pressure.

To carry out the process according to the invention, the dialkylcarbamic acid halides, especially the chlorides, are, in the case of process variant (a), preferably employed in an excess of 10 to 30 mol percent relative to the 4-hydroxy-pyrimidines. The reactants are in general dispersed in an organic diluent, and then heated to the boil under reflux for several hours, and thereafter the diluent is distilled off. In process variant (b) of the process according to the invention, the corresponding chloroformic acid esters are prepared from hydroxypyrimidines and phosgene, preferably in a molar ratio of 1:1 and in the presence of one of the above-mentioned acid acceptors, and these esters are reacted, preferably in situ, with secondary amines, either in the molar ratio of 1:1 in the presence of one of the above-mentioned acid acceptors, or with an excess of secondary amine. The individual process steps are in general carried out in organic diluents which are distilled off after the end of the reaction.

The new compounds are frequently obtained in the form of oils which in part cannot be distilled without decomposition but are freed from the last volatile constituents by so-called "incipient distillation", that is to say by prolonged heating under reduced pressure to moderately elevated temperatures, and are purified in this way. They are characterized by the refractive index. Some compounds are obtained in a crystalline form and are characterized by their melting point.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus* ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp.;

from the order of the Lepidoptera, for example Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima and Tortrix viridana;

from the order of the Coleoptera, for example Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica;

from the order of the Hymenoptera, for example Diprion spp., Hoplocampa spp., Lasius spp., Monomorium pharaonis and Vespa spp.;

from the order of the Diptera, for example Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa;

from the order of the Siphonaptera, for example Xenopsylla cheopis and Ceratophyllus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The following example illustrates the preparations of the novel compounds:

EXAMPLE 1

(A) The 4-hydroxypyrimidines to be used as starting materials could be prepared, for example, as follows:

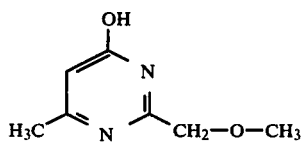 (a)

A solution of 60 g (1.1 mol) of sodium methylate in 200 ml of methanol was added dropwise to a solution of 80 g (0.5 mol) of 2-chloromethyl-4-hydroxy-6-methyl-pyrimidine [for its preparation, see T. Kato, H. Yamanaka and J. Kawamata, Yakugaku Zasshi 89, 460–464 (1969); Chemical Abstracts 71, 70653a (1969)] in 100 ml of methanol. The mixture was stirred for 2 hours at 55°–60° C. and then cooled to room temperature and brought to pH 5–6 with aqueous hydrochloric acid. After distilling off the solvent, the residue was dried at 70° C. and triturated with 800 ml of warm acetone, insoluble matter was filtered off and the filtrate was evaporated to dryness in vacuo. 60 g (78% of theory) of 2-methoxymethyl-4-hydroxy-6-methyl-pyrimidine remained in the form of colorless crystals of melting point 101° C.

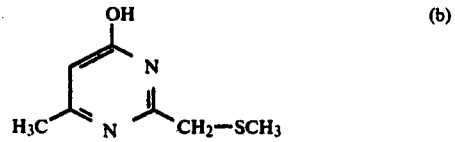 (b)

A mixture of 119 g (0.75 mol) of 2-chloromethyl-4-hydroxy-6-methylpyrimidine, 52.5 g (0.75 mol) of sodium methylmercaptide and 700 ml of acetonitrile was boiled under reflux for 3 hours. The hot reaction mixture was then filtered and the filtrate was evaporated to dryness in vacuo. This gave 68 g (53% of theory) of 2-methylthiomethyl-4-hydroxy-6-methyl-pyrimidine in the form of a beige powder of melting point 138° C.

The following compounds of the general formula

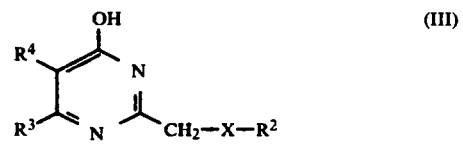 (III)

could be prepared analogously to (a) or (b).

TABLE 1

| Starting material | $R^2$ | $R^3$ | $R^4$ | X | Yield (% of theory) | Melting point °C. |
|---|---|---|---|---|---|---|
| c | $C_3H_7$-iso | $CH_3$ | H | O | 67 | 61 |
| d | $C_3H_7$-n | $CH_3$ | H | S | 86 | 87 |
| e | $CH_3$ | $CH_3$ | Cl | O | 88 | 142 |
| f | $C_3H_7$-iso | $CH_3$ | Cl | O | 51 | 206 (decomposition) |
| g | $CH_3$ | $CH_3$ | Br | O | 97 | 148 |
| h | $CH_3$ | $CH_3$ | Cl | S | 56 | 165 (decomposition) |
| i | $CH_3$ | $CH_3$ | $CH_3$ | S | 33 | 142 |
| j | $CH_3$ | $CH_3$ | Br | S | 58 | 137 |
| k | $CH_3$ | $CH_3$ | $CH_3$ | O | 89 | 112 |
| l | $C_2H_5$ | $CH_3$ | H | O | 84 | 68 |
| m | $C_2H_5$ | $CH_3$ | H | S | 56 | 132 |
| n | $C_2H_5$ | $CH_3$ | $CH_3$ | S | 43 | 122 |
| o | $CH_3$ | H | H | S | 51 | 182 |
| p | $CH_3$ | $CH_3$ | $C_2H_5$ | S | 71 | 144 |
| q | $CH_3$ | $CH_3$ | $C_3H_7$-iso | S | 45 | 86 |
| r | $CH_3$ | $C_4H_9$-tert. | H | S | 74 | 98 |
| s | $CH_3$ | $C_4H_9$-tert. | $CH_3$ | S | 55 | 82 |
| t | $CH_3$ | H | $CH_3$ | S | | |
| u | $CH_3$ | $CH_2$—$CH_2$—$CH_2$ | | S | 38 | 170 |
| v | $C_2H_5$ | $CH_2$—$CH_2$—$CH_2$ | | S | | |
| w | $C_3H_7$-n | $CH_3$ | $CH_3$ | S | | |
| x | $C_3H_7$-iso | $CH_3$ | $CH_3$ | S | | |
| y | $CH_3$ | $CH_3$ | $C_4H_9$-n | S | 39 | 107 |
| z | $CH_3$ | $CH_2$—$CH_2$—$CH_2$—$CH_2$ | | S | 71 | 154 |
| aa | $CH_3$ | $CH_3$ | $C_3H_7$-n | S | 61 | 127 |
| bb | $CH_3$ | H | $C_3H_7$-iso | S | | |
| cc | $CH_3$ | H | $C_2H_5$ | S | | |
| dd | $CH_3$ | H | $C_3H_7$-n | S | | |

TABLE 1-continued

| Starting material | R² | R³ | R⁴ | X | Yield (% of theory) | Melting point °C. |
|---|---|---|---|---|---|---|
| ee | CH₃ | H | C₄H₉-tert. | S | | |
| ff | C₂H₅ | H | C₃H₇-iso | S | | |

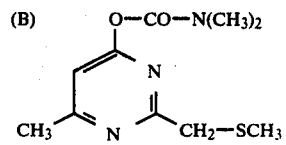
(B)

A mixture of 17 g (0.1 mol) of 2-methylthiomethyl-4-hydroxy-6-methylpyrimidine, 20.7 g (0.15 mol) of potassium carbonate, 200 ml of acetonitrile and 11.8 g (0.11 mol) of N,N-dimethylcarbamic acid chloride was boiled under reflux for 12 hours. After cooling to room temperature, the reaction mixture was filtered and the filtrate was then evaporated in vacuo. 18 g (75% of theory) of N,N-dimethyl-0-[2-methylthiomethyl-6-methyl-pyrimidin-4-yl]-carbamic acid ester remained in the form of a brown oil having a refractive index $n_D^{21}$ of 1.5541.

The following compounds of the formula

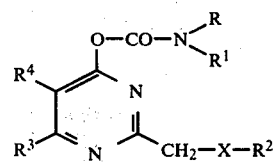
(I)

could be prepared analogously:

The activity of the compounds of this invention is illustrated by the following example wherein the compounds according to the present invention are each identified by the number (given in brackets) from Example 1(B).

EXAMPLE 2

Doralis test (systemic action)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were each watered with 20 ml of the preparation of the active compound, of the desired concentration, so that this preparation penetrated into the soil without wetting the shoot. The active compound was taken up by the roots and passed on into the shoot.

After the desired time, the destruction was determined.

The following compounds showed an activity superior to that of the prior art compounds: (1), (10), (9), (7), (8), (5), (11) and (12).

TABLE 2

| Compound No. | R | R¹ | R² | R³ | R⁴ | X | Yield (% of theory) | Physical data (refractive index; melting point,°C.) |
|---|---|---|---|---|---|---|---|---|
| 2 | CH₃ | CH₃ | CH₃ | CH₃ | H | O | 84 | $n_D^{24}$:1.5048 |
| 3 | CH₃ | CH₃ | CH₃ | CH₃ | Br | O | 46 | 76 |
| 4 | CH₃ | CH₃ | C₃H₇-iso | CH₃ | H | O | 83 | $n_D^{24}$:1.4998 |
| 5 | CH₃ | CH₃ | CH₃ | CH₃ | Cl | O | 42 | 57 |
| 6 | CH₃ | CH₃ | C₃H₇-n | CH₃ | H | S | 93 | $n_D^{22}$:1.5756 |
| 7 | CH₃ | CH₃ | CH₃ | CH₃ | Br | S | 69 | $n_D^{22}$:1.5305 |
| 8 | CH₃ | CH₃ | CH₃ | CH₃ | CH₃ | O | 71 | 45 |
| 9 | CH₃ | CH₃ | CH₃ | CH₃ | Cl | S | 73 | $n_D^{23}$:1.5585 |
| 10 | CH₃ | CH₃ | CH₃ | CH₃ | CH₃ | S | 75 | 47 |
| 11 | CH₃ | CH₃ | C₂H₅ | CH₃ | H | S | 76 | $n_D^{20}$:1.5042 |
| 12 | CH₃ | CH₃ | C₂H₅ | CH₃ | CH₃ | S | 89 | $n_D^{20}$:14957 |
| 13 | CH₃ | CH₃ | C₂H₅ | CH₃ | H | O | 72 | $n_D^{20}$:1.5245 |
| 14 | CH₃ | CH₃ | CH₃ | H | H | S | 94 | $n_D^{21}$: 1.5412 |
| 15 | C₂H₅ | C₂H₅ | CH₃ | CH₃ | CH₃ | S | 82 | $n_D^{21}$: 1.5156 |
| 16 | CH₃ | CH₃ | CH₃ | CH₃ | C₂H₅ | S | 87 | $n_D^{20}$: 1.5373 |
| 17 | CH₃ | CH₃ | CH₃ | CH₃ | C₃H₇-iso | S | 89 | 73 |
| 18 | CH₃ | CH₃ | CH₃ | C₄H₉-tert. | H | S | 78 | $n_D^{21}$: 1.5218 |
| 19 | CH₃ | CH₃ | CH₃ | C₄H₉-tert. | CH₃ | S | 76 | $n_D^{21}$: 1.5173 |
| 20 | CH₃ | CH₃ | CH₃ | H | CH₃ | S | | |
| 21 | CH₃ | CH₃ | CH₃ | CH₂—CH₂—CH₂ | | S | 75 | 63 |
| 22 | CH₃ | CH₃ | C₂H₅ | CH₂—CH₂—CH₂ | | S | | |
| 23 | CH₃ | CH₃ | C₃H₇-n | CH₃ | CH₃ | S | | |
| 24 | CH₃ | CH₃ | C₃H₇-iso | CH₃ | CH₃ | S | | |
| 25 | CH₃ | CH₃ | CH₃ | CH₃ | C₄H₉-n | S | 85 | $n_D^{21}$:1. 5252 |
| 26 | CH₃ | CH₃ | CH₃ | CH₂—CH₂—CH₂—CH₂ | | S | 68 | 69 |
| 27 | CH₃ | CH₃ | CH₃ | CH₃ | C₃H₇-n | S | 99 | $n_D^{21}$: 1.5307 |
| 28 | CH₃ | CH₃ | CH₃ | H | C₃H₇-iso | S | | |
| 29 | CH₃ | CH₃ | CH₃ | H | C₂H₅ | S | | |
| 30 | CH₃ | CH₃ | CH₃ | H | C₃H₇-n | S | | |
| 31 | CH₃ | CH₃ | CH₃ | H | C₄H₉-tert. | S | | |
| 32 | CH₃ | CH₃ | C₂H₅ | H | C₃H₇-iso | S | | |

What we claim is:

1. An N,N-dialkyl-0-(2-substituted-methyl-pyrimidin-4-yl)-carbamic acid ester of the formula

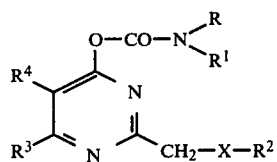

in which
R, $R^1$ and $R^2$ each independently is alkyl,
X is oxygen or sulphur,
$R^3$ is hydrogen or alkyl, and
$R^4$ is hydrogen, alkyl or halogen, or
$R^3$ and $R^4$ conjointly form an alkylene bridge.

2. An ester according to claim 1 in which
R, $R^1$ and $R^2$ each independently is alkyl with 1 to 6 carbon atoms,
$R^3$ is hydrogen or alkyl with 1 to 8 carbon atoms, and
$R^4$ is hydrogen, alkyl with 1 to 6 carbon atoms, chlorine or bromine, or
$R^3$ and $R^4$ conjointly form an alkylene group with 3 to 5 carbon atoms.

3. An ester according to claim 1, wherein such ester is N,N-dimethyl-0-(2-methylthiomethyl-6-methyl-pyrimidin-4-yl)-carbamic acid ester of the formula

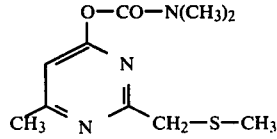

4. An ester according to claim 1, wherein such ester is N,N-dimethyl-0-(2-methylthiomethyl-5,6-dimethyl-pyrimidin-4-yl)-carbamic acid ester of the formula

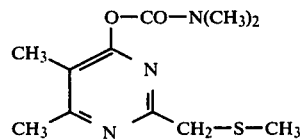

5. An ester according to claim 1, wherein such ester is N,N-dimethyl-0-(2-methoxymethyl-5,6-dimethyl-pyrimidin-4-yl)-carbamic acid ester of the formula

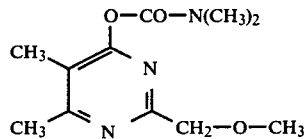

6. An ester according to claim 1, wherein such ester is N,N-dimethyl-0-(2-ethylthiomethyl-6-methyl-pyrimidin-4-yl)-carbamic acid ester of the formula

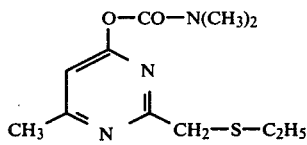

7. An ester according to claim 1, wherein such ester is N,N-dimethyl-0-(2-ethylthiomethyl-5,6-dimethyl-pyrimidin-4-yl)-carbamic acid ester of the formula

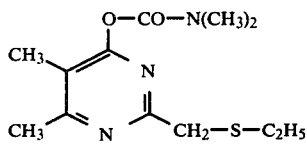

8. An arthropodicidal composition containing as active ingredients an arthropodicidally effective amount of an ester according to claim 1 in admixture with a diluent.

9. A method of combating arthropods which comprises applying to the arthropods, or to a habitat thereof, an arthropodicidally effective amount of an ester according to claim 1.

10. The method according to claim 9, in which said ester is
N,N-dimethyl-0-(2-methylthiomethyl-6-methyl-pyrimidin-4-yl)-carbamic acid ester,
N,N-dimethyl-0-(2-methylthiomethyl-5,6-dimethyl-pyrimidin-4-yl)-carbamic acid ester,
N,N-dimethyl-0-(2-methoxymethyl-5,6-dimethyl-pyrimidin-4-yl)-carbamic acid ester,
N,N-dimethyl-0-(2-ethylthiomethyl-6-methyl-pyrimidin-4-yl)-carbamic acid ester, or
N,N-dimethyl-0-(2-ethylthiomethyl-5,6-dimethyl-pyrimidin-4-yl)-carbamic acid ester.

* * * * *